United States Patent [19]
Fraser et al.

[11] Patent Number: 4,571,834
[45] Date of Patent: Feb. 25, 1986

[54] KNEE LAXITY EVALUATOR AND MOTION MODULE/DIGITIZER ARRANGEMENT

[75] Inventors: Gregory A. Fraser, Montreal; Simon Raab, Lorraine, both of Canada

[73] Assignee: Orthotronics Limited Partnership, Canada

[21] Appl. No.: 735,080

[22] Filed: May 16, 1985

Related U.S. Application Data

[62] Division of Ser. No. 581,432, Feb. 17, 1984.

[51] Int. Cl.$^4$ .......................... G01C 1/08; G01B 7/00
[52] U.S. Cl. .................................... 33/1 PT; 33/512; 128/782
[58] Field of Search ............... 33/1 PT, 511, 512, 520; 128/782

[56] References Cited

U.S. PATENT DOCUMENTS 4,306,571 12/1981 McLeod, Jr. ................. 128/782
4,436,099 3/1984 Raftopoulos ................. 128/782
4,486,955 12/1984 Fisher et al. ................. 33/1 PT

FOREIGN PATENT DOCUMENTS

2754500 6/1978 Fed. Rep. of Germany ........ 33/520

Primary Examiner—Willis Little
Attorney, Agent, or Firm—Fishman & Dionne

[57] ABSTRACT

The invention relates to a knee laxity evaluator which consists of an instrumented seat, a restraint means for restraining the thigh of a patient to the instrumented seat, a motion module for measuring motion of the unrestrained part of the leg relative to the thigh of the patient, and processor means for analyzing outputs of the instrumented seat and the motion module to provide indications of applied force and relative motion. The invention also relates to a specific motion module/digitizer combination which can be used as a part of the knee laxity evaluator, or which can be used independently or in alternate systems. The invention also relates to a novel dynanometer for use in the knee laxity evaluator which includes a triple beam arrangement.

6 Claims, 14 Drawing Figures

KNEE LAXITY EVALUATOR AND MOTION MODULE/DIGITIZER ARRANGEMENT

This application is a division of application Ser. No. 581,432, filed Feb. 17, 1984.

BACKGROUND OF INVENTION (a) Field of the Invention

The invention relates to a novel knee laxity evaluator (KLE) system.

The invention also relates to a motion module/digitizer combination which can be used in the KLE, or which can be used independently or in other systems. More specifically, the invention relates to such a combination which can measure, in three dimensional space, and relative to the position of a first point or body or co-ordinate system, position or motion of a second point or body, as well as position or motion of the second point or body relative to a third, fourth, fifth . . . nth points, or positions of the second body, or combinations thereof.

(b) Description of Prior Art

Currently, the practice of measuring knee laxity is limited to a subjective evaluation by a physician of relative displacements at the knee. Through such an examination, damage to ligaments could be ascertained as a function of excess laxity or joint movement during passive loading by the physician. The limitations of this technique are: (a) a high level of subjectivity; (b) no quantitative or reproducible results; (c) no knowledge of applied forces; and (d) there are complicated motions which cannot be evaluated by human feel alone and hence there is important information being lost.

In accordance with the present invention, a KLE includes a motion module, that is, a module for measuring, in three dimensional space, movement of a point or body relative to a fixed point or body. Modules of this type are known in the art as is illustrated, for example, in U.S. Pat. No. 3,944,798, Eaton, Mar. 16, 1976, U.S. Pat. No. 4,057,806, Furnadjiev et al, Nov. 8, 1977, and U.S. Pat. No. 4,205,308, Haley et al, May 27, 1980.

Electrical and electronic digitizers are also known in the art. For example, a two dimensional digitizer is illustrated in U.S. Pat. No. 3,956,588, Whetstone et at, May 11, 1976.

However, there are no teachings in the art for combining the first systems, usually referred to as motion modules, and digitizers, whereby it is possible to measure the position or motion of a second point or body relative to the position of a first point or body and also relative to third, fourth, fifth . . . nth points or positions of the second body or combinations thereof.

SUMMARY OF INVENTION

It is therefore an object of the invention to provide a novel knee laxity evaluator system.

It is a further object of the invention to provide a knee laxity evaluator system which uses a motion module.

It is a still further object of the invention to provide a combined electronic motion module/digitizer combination which can be used in the KLE or which can be used independently or in other systems.

It is a still further object of the invention to provide a novel dynamometer which can be used in the KLE or which can be used independently.

It is a more specific object of the invention to provide such a combination which will measure, in three dimensional space, and relative to the position of a first point or body, position or motion of a second point or body as well as position or motion of the second point or body relative to the third, fourth, fifth . . . nth points, or positions of the second body or combinations thereof.

In accordance with a particular embodiment of the invention, a knee laxity evaluator comprises an instrumented seat for seating a patient and restraint means for restraining a portion of the patient to the instrumented seat whereby to measure forces applied to the patient at an unrestrained part thereof. Motion module means measure the motion of the unrestrained part of the patient relative to the restrained part thereof, and processor means analyze outputs of the instrumented seat and the motion module means and provide indications of applied force and motion of the unrestrained part relative to the restrained part.

From a different aspect, and in accordance with the invention, a motion module/digitizer combination comprises an elongated member having a first end and a second end and comprising a first link arm and a second link arm and means movably connecting the first link arm to the second link arm so as to permit translational motion between the first end and the second end, the means for connecting being disposed intermediate the first and second ends, the means also including first transducer means for measuring the translational motion. First mounting means are provided at the first end for mounting the first end at a first point, body or co-ordinate system and second mounting means are provided at the second end for mounting the second end at a second point or body. Second transducer means are provided at the first end for measuring three dimensional rotational motion of the first link arm relative to the first point or body and a third transducer means is provided at the second end for measuring three dimensional rotational motion of the second link arm relative to the second point or body. In accordance with the invention, a portion of the second link arm is detachable from the remainder of the second link arm and the second mounting means and means are connectable to the remainder of the second link arm. Whereby, the combination of the first link arm, the remainder of the second link arm, and the means connectable, can be used to measure the position in space of third, fourth, fifth . . . nth points or combinations thereof. And whereby, when the remainder of the link arm is reattached to the portion of the second link arm and the second mounting means, measurements can be performed to determine the position in space of the second point or body relative to the position of the first point or body or the position in space of the second point or body relative to the third, fourth, fifth . . . nth points or positions of the second body or combinations thereof.

From a still different aspect, and in accordance with the invention, there is provided a dynamometer for determining the magnitude and direction of an applied force. The dynamometer includes three spaced beams and support means on each of the beams. Platform means are disposed on and supported by the support means for receiving and being deflected by the applied force. The deflection of the platform is transmitted to the beams to cause deflection of the beams. Means are provided for measuring the deflection of the beams in two directions thereof. In accordance with the invention, the beams are arranged such that no two redundant directions of deflection of the beams are permissible.

BRIEF DESCRIPTION OF DRAWINGS

The invention will be better understood by an examination of the following description, together with the accompanying drawings, in which.

DESCRIPTION OF PREFERRED EMBODIMENTS

Turning first to FIGS. 1 to 5, there is illustrated a patient 1 having the KLE attached and being examined by a physician 3. The KLE system includes a thigh restraint means 7, an instrumented seat 9 and a motion module 11. The motion module is connected at one end 13 to the instrumented seat which, as will be seen below, constitutes a fixed point or body. The other end 15 is connected to a second point or body. The purpose of the instrument is to determine the movement of the second point or body relative to the first point or body in three dimensional space.

Figure 1:
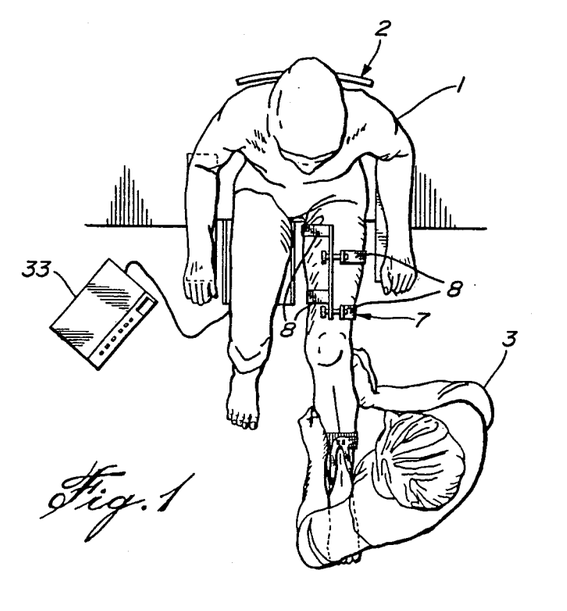
FIG. 1 is a three dimensional view of a patient, with KLE attached, being examined by a physician.
Figure 2:
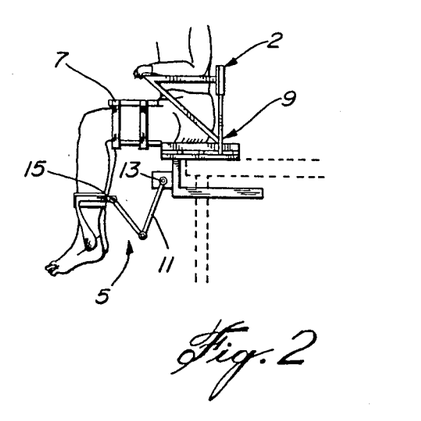
FIG. 2 is a side view of the patient.
Figure 3:
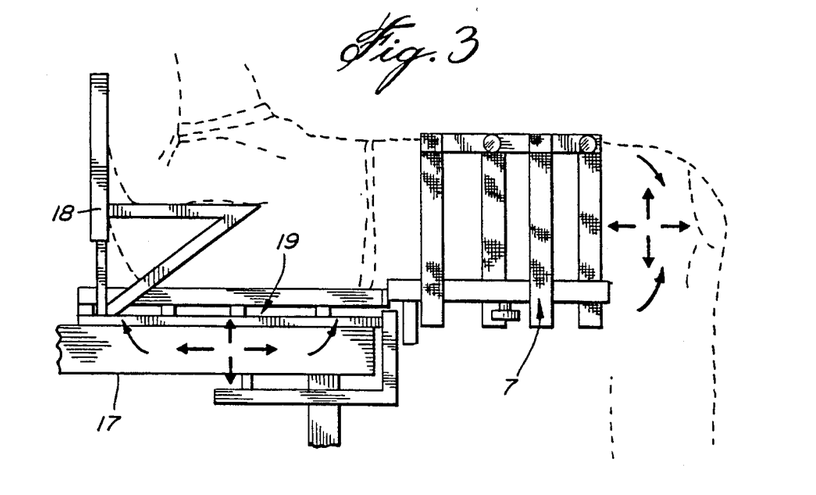
FIG. 3 is a more detailed side view of the patient.

The instrumented seat may be mounted on an examining table 17 and consists of a dynanometer 19 which measures applied forces. Instruments for measuring force are described in MEASUREMENT SYSTEMS: APPLICATION AND DESIGN by E. O. Doebelin, McGraw Hill, pps 333–350. The instrumented seat may also have an adjustable seat back arrangement 18 as is well known in the art.

The thigh restraint 7 comprises two or more pairs of off-set straps, which are fastened to each other by fastening means 8, and which displace soft tissue and may also provide a torquing of the tissue about the femur in order to minimize movement of the femur relative to the seat.

Figures 4, 5:
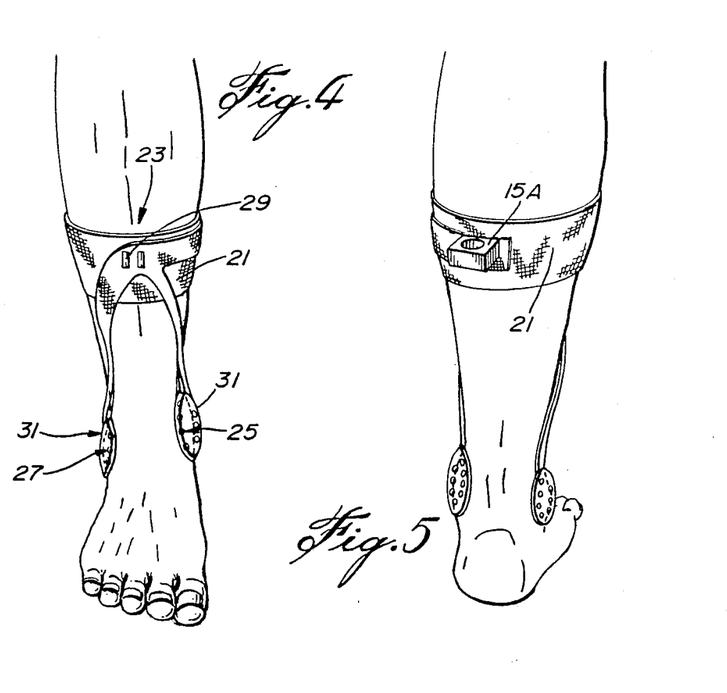
FIG. 4 is a front view of the leg showing motion/module digitizer attachment.
FIG. 5 is a rear view of the leg showing the electrogoniometer attachment.

The lower leg attachment, illustrated best in FIGS. 4 and 5, comprises a strap member 21, for example a velcro strap on which is carried the attachment 15a for the end 15 of the motion module. The lower leg attachment functions by referencing the motion module to three bony prominences of the lower leg, namely, the tibial crest 23 and the medial and lateral malleoli, 25 and 27 respectively. Rollers 29 align themselves to the bony contours of the tibial crest, and balls in malleolar cups 31 do the same at the malleoli. These balls and rollers allow the skin to move between the attachment of the bone so that the attachment will move only with the bone which is important in attaining a true bone position measurement.

The system also includes a microprocessor based monitor 33 which receives outputs from the dynanometer and the motion module. Thus, the KLE is capable of sensing and measuring applied loads and displacements existing during the use of all standard knee evaluation techniques. In addition, the present KLE is designed to minimize the effects of soft tissue while still permitting the physician to hold, palpate and manipulate the joint as in normal procedures while the KLE provides accurate applied force and tibial-femoral motion readings in displayed and printed form.

The dynanometer force plate measures forces and moments in basic directions and permits the physician to know exactly to what levels the knee is being stressed. This is important when measuring laxity since the amount of relative bone motion depends on the stress applied. Knowledge of the forces is of utmost importance to the objective interpretation of joint laxity.

The motion module measures the true three dimensional position of the tibia relative to the seat, and hence, as the thigh is restrained, to the femur.

The motion module is an electromechanical device which functions on the principle that at least six measurements are required to totally define the position of an object in space as will be further discussed below. It will consist of a means capable of measuring six degree of freedom, three dimensional motion of one point or body relative to another point or body and preferably comprises a unique arrangement of electronic components capable of measuring rotational or translational displacements. A specific module is described below in association with FIGS. 6 to 8. Generally speaking, the two points or bodies between which relative motions are being measured are connected by a single rigid telescopic arm, or a single arm having a joint between its two ends.

The force measurement on the dynanometer is accomplished through the principles of opposite and equal reaction forces. The forces applied to the knee of the patient are reacted to by the femur and thigh which are in turn transmitted to the dynanometer. In as much as the forces are of a different arrangement in the dynanometer as compared to the knee, knowledge of the relative position of the relative position of the knee and the dynanometer, provided by the motion module, permits a theoretical interpretation of the forces and their representation in the co-ordinate system of the knee.

In operation, a patient is seated in the instrumented seat and the thigh of the leg of interest is restrained as shown in FIG. 1. The lower leg attachment is then mounted on the same leg as illustrated in the drawings, and the motion module is connected between the seat and the lower leg attachments. The physician can then twist the lower leg, and he will receive outputs indicating relative displacement as well as force applied.

Figure 6:
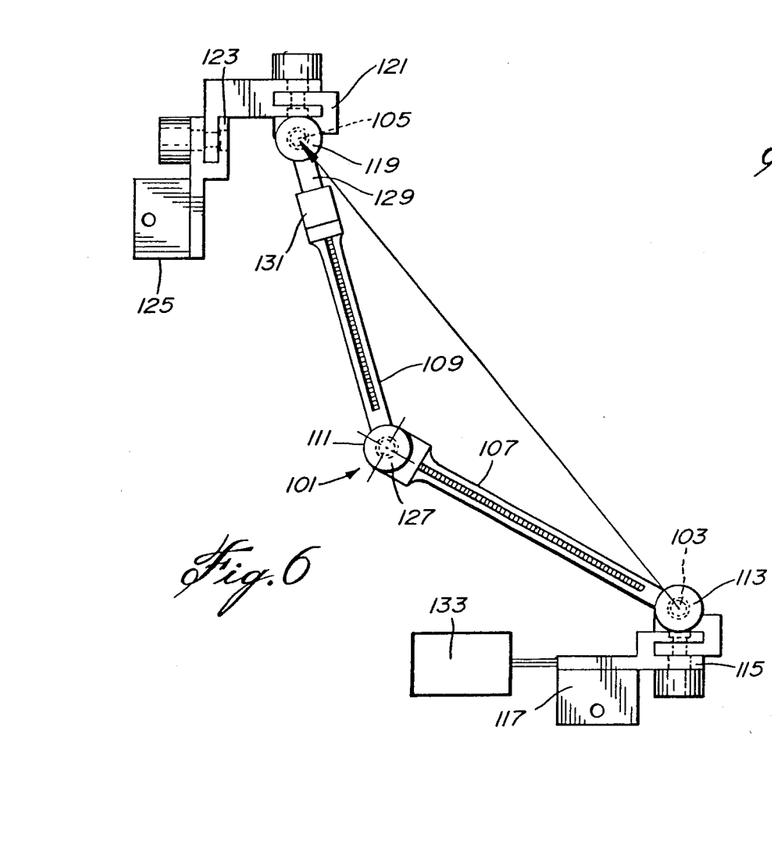
FIG. 6 is a front view of an electronic motion module/digitizer combination in accordance with the invention.
Figure 7:
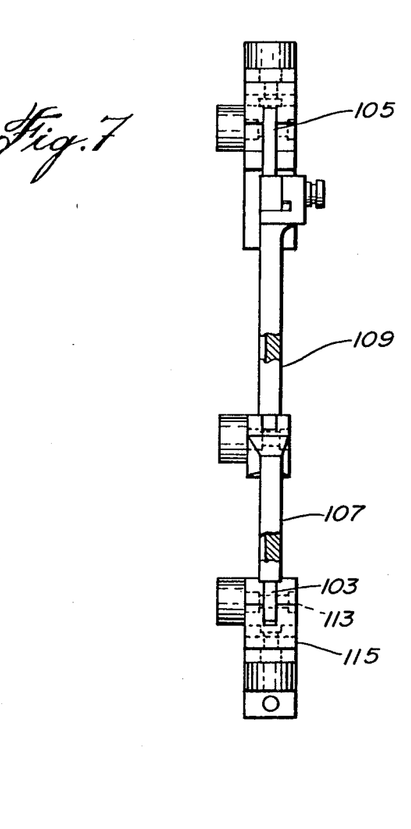
FIG. 7 is a side view of the combination.

Turning now to FIGS. 6 to 8, there is illustrated a particular motion module/digitizer combination which can be used in the KLE environment. However, as also mentioned, the combination can be used in other systems or it can be used independently. For example, it could be used in association with machine tools and other mechanical systems where it is necessary to be able to measure displacement of a first point or body relative to a second point or body.

To measure the motion of a body in three dimensional space, six unique measurements are required relating to the six degrees of freedom of motion in three dimensional space. The measurements can constitute six unique rotational measurements or six unique translational measurements or combinations thereof, i.e., four rotational and two translational, etc. The combination in accordance with the invention takes five unique measurements of rotational motion and one measurement of translational motion.

Referring now to FIGS. 6 and 7, the combination includes an elongated member 101 having a first end 103 and a second end 105. The elongated member comprises a first link arm 107 and a second link arm 109. The link arms 107 and 109 are joined together at 111 to permit relative translational movement as between 103 and 105 and to measure this translational movement. In the embodiments illustrated, the link arms are connected for pivotal motion whereby to permit relative translational motion of 103 and 105, and a rotary transducer means is used to measure this translational motion as will be discussed below.

As will be obvious, other means could be used for so connecting arms 107 and 109. For example, one of the arms could include a sleeve for overlying the other arm and for permitting movement of the other arm into and out of the sleeve. A translational transducer means could be included in the sleeve for measuring the translational motion.

Examples of rotary transducer means which can be used are resistive potentiometers, variable inductance transformers, syncro resolvers, inductance potentiometers and variable reluctance transducers. Examples of translational transducers which could be used are dial indicators, resistive potentiometers, variable inductance transformers, capacitance transducers, piezoelectric transducers, ionization transducers and optical transducers.

In describing the illustrated embodiment, rotary and translational potentiometers, respectively, are utilized. Accordingly, these will be henceforth referred to. However, it is to be understood that such translational and rotary potentiometers could be replaced by respective ones of the above-mentioned transducers.

Disposed at the end 103 is a first rotary potentiometer 113 which is disposed in line with the arm 103 and rotatable about an axis at right angles to the arm 103. A second rotary potentiometer 115 is disposed at right angles to the potentiometer 113 and is rotatable about an axis at right angles to the axis of the potentiometer 113. Potentiometer 115 is mounted on mounting block 117 for mounting the arrangement at one end thereof.

Disposed at second end 105 is a third rotary potentiometer 119 which is in line with the second link arm 109 and which rotates about an axis at right angles to the second link arm 109. A fourth rotary potentiometer 121 is disposed at right angles to potentiometer 119 and is rotatable about an axis at right angles to the axis of potentiometer 119. A fifth rotary potentiometer 123 is also disposed at right angles to potentiometer 119 and is rotatable about an axis at right angles to the axis of potentiometer 119. Potentiometer 123 is also at right angles to potentiometer 121 and its axis of rotation is also at right angles to the axis of potentiometer 121.

Potentiometer 123 is connected to mounting block 25 for mounting the arrangement at a second point.

In the illustrated embodiment, arms 107 and 109 are connected at 111 by a sixth rotary potentiometer 127 which is in line with both arms 107 and 109 and whose axis of rotation is at right angles to both arms 107 and 109.

The arrangement as thus far described can measure the motion in three dimensional space of end 105 relative to end 103 or vice-versa and is referred to as motion module. In accordance with the invention, there is provided the potential for digitizing the positions of third, fourth, fifth . . . nth points or bodies (henceforth, the use of the term points will be used and understood to refer to points or bodies) in three dimensional space, or combinations thereof, and of then measuring the motion or position of one of the points 103 and 105 relative to the position of the other point or relative to the third, fourth, fifth . . . nth points, or positions of the second body, or combinations thereof. This potential is achieved by making one of the link arms disconnectable from its respective mounting block and reconnectable again thereto. In the illustrated embodiment, link arm 109 is disconnectable from mounting block 125. Specifically, the protrusion 129 which extends from potentiometer 119 is insertable into a receptacle 131. The protrusion is also removable from the receptacle, and other inserts, such as those illustrated in FIGS. 8A, 8B, etc. can be inserted into the receptacle for digitizing the positions of other points in space.

For an understanding as to how the combination operates, we will take the intersection of the axes of potentiometers 113 and 115 as the global origin 0. Thus, potentiometers 113, 115 and 127 define a spherical coordinate system about 0. Specifically, potentiometers 113 and 115 provide the conventional angles $\theta$ and $\phi$ respectively, while the potentiometer 127, combined with 107 and 109, provide the length of the vector R. (Knowing the length of 107 and 109, and knowing the angle therebetween, it is quite easy to determine the length of the vector R). Point B is defined as the intersection of the axes of potentiometers 119, 121 and 123 and is considered the origin of the "moving body" coordinate system. In distinction thereto, 0 is considered the origin of a "fixed" body or co-ordinate system. Specifically, mounting block 125 would be mounted on a moving body. Mounting block 117 would be mounted on the fixed body or co-ordinate system, and the measurement of the movement of 105 relative to 103 would define the motion of the moving body relative to the fixed body or co-ordinate system.

The final description of the moving body motion is contained in the three finite rotations provided by the potentiometers 119, 121 and 123.

To illustrate how the combination is used as a digitizer, the protrusion 119 is removed from the receptacle 131, and one of the digitizer tips illustrated in FIG. 8 is inserted into the receptacle in place of the protrusion 119. The tip is then pointed at points of interest, namely, a third, fourth, fifth . . . nth points above-mentioned, and a reading is taken of the three dimensional position in space of these points.

As will be understood, conductive leads from the potentiometers will be brought to a connecting board, which could be disposed on the mounting blocks 117, so that the electrical signals developed at the potentiometers can be brought to a processing means such as the processing means illustrated schematically at 133 in FIG. 1. It will, of course, be necessary to provide DC power to the potentiometer to measure the changing resistance thereof, as well known in the art, and this DC power could also be provided from the processing means 133.

The potentiometers will provide the data for determining the extent and direction of the motion of point 105. In order to determine the direction and extent, the data must be processed. Preferably, the data is processed by computer means. A flow chart for controlling such a computer is illustrated in FIG. 8.

Figure 9:
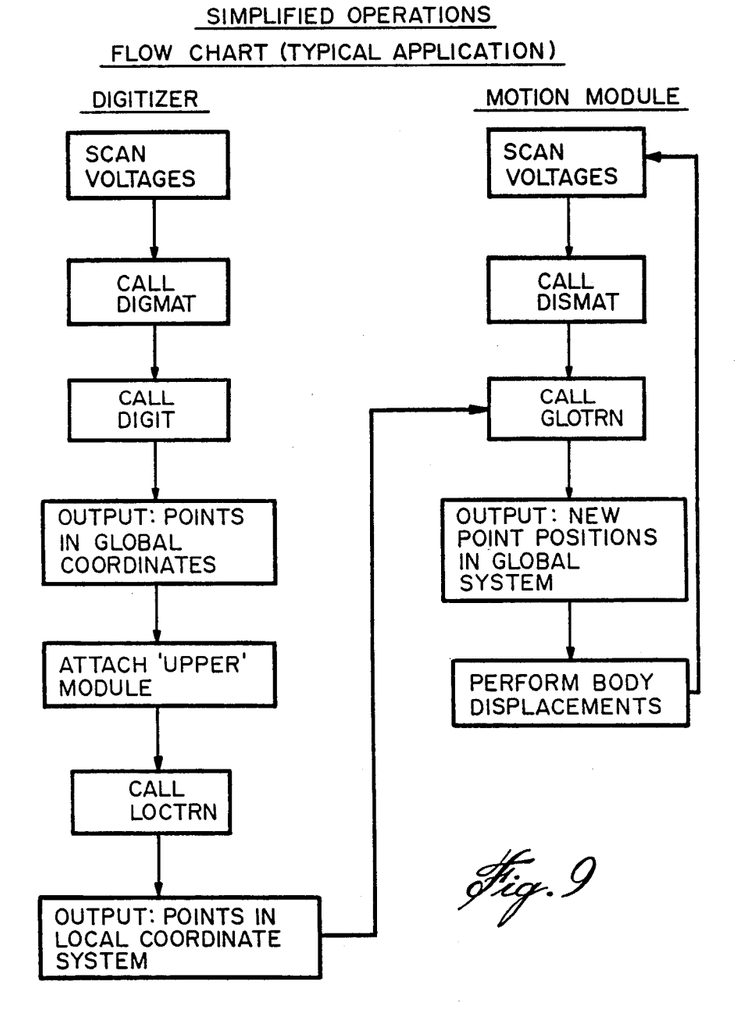
FIG. 9 is a flow chart of software for processing the electrical outputs of the combination to achieve the desired results.

Three basic subroutines are employed in digitization, two of which are illustrated in the flow chart. The DIGMAT (digitization transformation matrix) and DIGIT (digitization) are shown in the flow chart while the NEWTIP (support routine for user defined tip) must be provided by the user and takes into account the dimensions and shape of the user supplied tip.

While the user must write a program employing the subroutines in a manner appropriate to his specific application, in all cases the following procedure must be used.

The protrusion 129 is removed from the receptacle 131, and one of a variety of tips is inserted in the receptacle. The mounting blocks 117 must be firmly mounted at a position which both permits easy access to most points of interest and is also appropriate for any subsequent motion measurement using both upper and lower components of the motion module. A position of interest is then pointed at with the tip.

The physical characteristics are inputted into the computer memory, and a code is then presented to the computer to let it know which of the tips is being used.

Upon pointing at the position with the tip, the program must be activated either through a remote switch or a keyboard entry. The control program will then scan the signals in the potentiometer, and then, in sequence, call the subroutine DIGMAT, which uses as input the voltage values of potentiometers 113, 115 and 127, as well as the voltage of the power supply. DIGMAT outputs to transformation matrices which are used in the subroutine digit which is the next subroutine to be called. DIGIT actually computes the position of DTIP in the global coordinate system using as input the output of DIGMAT and DTIP coordinates in potentiometer 127 coordinate system.

An output is then provided of the points in the global coordinate system, that is, relative to the point 0.

This procedure is repeated until all of the points of interest have been digitized. The TIP is then removed from the receptacle 131 and the protrusion 129 is again inserted in the receptacle. The subroutine LOCTRN, which computes the coordinates of the digitized points in the local coordinate system (that is, with the point B as an origin) is then called. These points are then outputted to the GLOTRN subroutine which will be discussed below.

In the meantime, the mounting block 125 would have been attached to a point of interest. Displacements of this point are performed, and the potentiometer signals are once again scanned. This data is communicated to the computer and the subroutine DISMAT is called. DISMAT computes the contents of the transformation matrix describing the body in three dimensional space. The subroutine GLOTRN is then called and outputs new positions of those points previously digitized on the body or analytically generated points, in the global system. This procedure continues as the point of interest moves through different positions.

The following are the technical specifications of the subroutines:

SUBROUTINE DIGMAT (DVOL, DT12, DT3)

Description

This subroutine computes matrix DT12 as well as matrix DT3 which locates the position of potentiometer-113 and potentiometer-127 coordinate systems, respectively.

These two matrices are strictly inputs to subroutines DIGIT and NEWTIP, and have no significance to the user.

Input

DVOL (4), voltages of potentionmeters-115, 113 and 127, and the power supply, respectively. (Note 1)

Output

DT12 (3,3) and DT3 (3,3) are the abovementioned matrices. (Note 1)

Note

1—all the variable names starting with D in each subroutine, are double precision.

SUBROUTINE DIGIT (DT12, DT3, DTIP, DPNTRF)

Description

This subroutine computes the coordinates of the digitizer tip with respect to the global coordinate system.

Input

DT12 (3,3), and DT3 (3,3) locate the position of potentiometer-113 and potentiometer-127 coordinate systems, respectively. (Refer to subroutine DIGMAT). (Note 3)

DTIP (3) are the coordinates of the tip in use with respect to the potentiometer-127 coordinate system. (Note 1, 2 and 3)

Output

DPNTRF (3) are the coordinates of the tip with respect to the global coordinate system. (Note 2 and 3)

Notes

1—The coordinates of the digitizer tips are provided as part of the Digitizer Unit. For the coordinates of User tip, use subroutine NEWTIP. (Refer to subroutine NEWTIP)

2—In all coordinate arrays 1, 2 and 3 are X, Y and Z coordinates, respectively. (e.g. DTIP (1)=X coordinate)

3—All variable names starting with D are in Double Precision.

SUBROUTINE NEWTIP (DT12, DT3, DPNTRF, DTIP)

Description

Figure 8A:
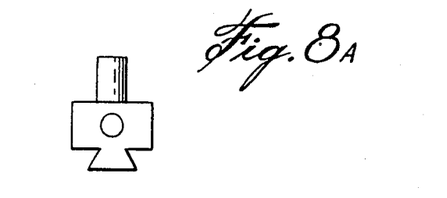
FIG. 8 illustrates examples of inserts.
Figure 8B:
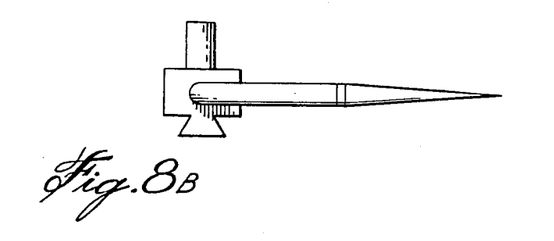
Figure 8C:
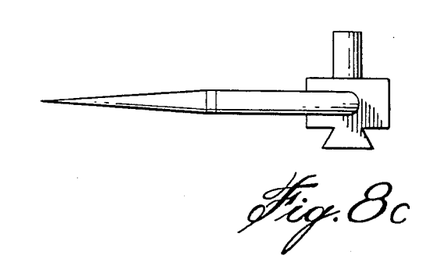
Figure 8D:
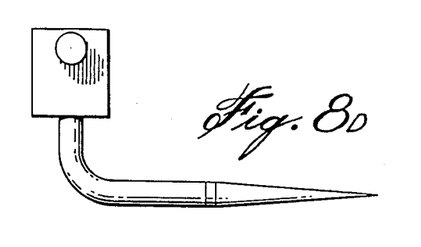

The main purpose of this subroutine is to define the coordinates of any user-designed tip with respect to potentiometer-127 coordinate system without independently measuring the tip dimensions. In order to find the tip constants, first mount tip number 1 (see 8b) and touch a point (Note 1). Then mount the new tip and touch the same point. Through the software the coordinates of the point are computed by tip number 1 and are used to compute the constants for the new tip. (Refer to the Control Program Flow Chart).

Notes

1—For best results, use a point within 6 and 8 inches from the base of the digitizer.

Input

DT12 (3,3), and DT3 (3,3) locate the position of potentiometer-113 and potentiometer-127 coordinate systems, respectively. (Note 1)

DPNTRF (3): coordinates of the digitized point by tip number 1 with respect to global coordinate system. (Note 1 and 2)

Output

DTIP(3): coordinates of the tip with respect to potentiometer-127 coordinate system, or better known as the new tip constants. (Note 1 and 2)

Notes

1—All variable names starting with D are double precision.
2—In the coordinate system arrays 1, 2 and 3 are X, Y and Z coordinates, respectively.

SUBROUTINE DISMAT (DVOL, DMAT2)

Description

DISMAT computes the position of the local coordinate system with respect to the global coordinate system. The local coordinate system is in line with indicated edges of upper mounting block.

Input

DVOL(7) voltage readings of potentiometers-113, 127 115, 119, 121, 123 and the power supply line, respectively. (Note 1)

Output

DMAT2 (4,3) consists of:
DMAT2 (4,1), DMAT2 (4,2) and DMAT2 (4,3) are the coordinates of point B in global coordinate system.
DMAT2 (3,3) defines the position of the local coordinates system with respect to the global coordinate system. (Note 1)
DMAT 2 (4,3) is input only to subroutines LOCTRN and GLOTRN, and has no significance to the user.

Note

1—All variable names starting with D are double precision.

SUBROUTINE LOCTRN (DMAT2, DPOINT, DPNTLC, N)

Description

LOCTRN computes the coordinates of the digitized points in local coordinate system.

These coordinates are constant as long as the upper mounting block is fixed to the bone or some other chosen mounting base.

If the upper mounting block is shifted these coordinates should be computed again by calling subroutine LOCTRN. (Refer to the Control Program Flow Chart)

Input

DMAT2 (4,3), from subroutine DISMAT (refer to subroutine DISMAT). (Note 1)
N is number of points; integer DPOINT (3,N): coordinates of the digitized and analytical points in the global coordinate system. (Note 1 and 2)

Output

DPNTLC (3,N) coordinates of the points with respect to the local coordinate system. (Note 1 and 2)

Note

1—All variable names starting with D are double precision.
2—In the coordinates arrays 1, 2 and 3 are X, Y and Z coordinates, respectively.

SUBROUTINE GLOTRN (DAMT2, DPNTLC, DPNTGL, N)

Description

GLOTRN computes the new coordinates of the points in the global coordinate system.

Input

DMAT 2 (4,3), from subroutine DISMAT (refer to subroutine DISMAT). (Note 1)
N number of points; integer.
DPNTLC (3,N): coordinates of the points in local coordinate system. (Note 1 and 2)

Output

DPNTGL (3,N) new coordinates of the points in global coordinate system. (Note 1 and 2)

Notes

1—All variable names starting with D are double precision.
2—In the coordinate arrays 1, 2 and 3 are X, Y and Z coordinates, respectively.

Figure 10:
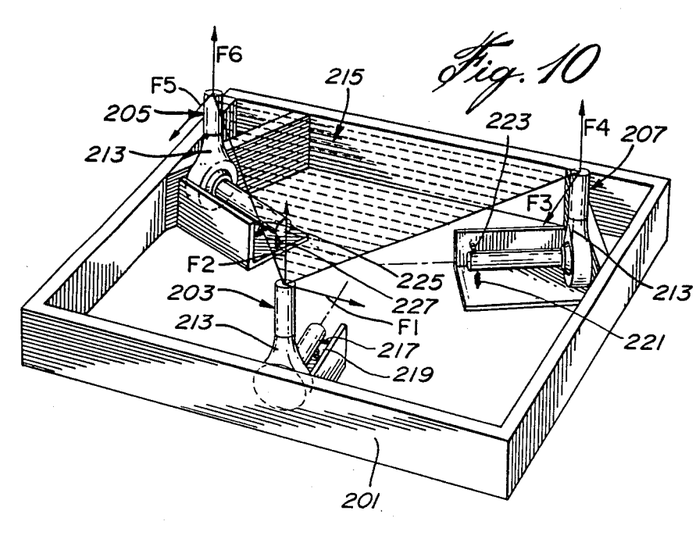
FIG. 10 illustrates a dynanometer in accordance with a further aspect of the invention.
Figure 11:
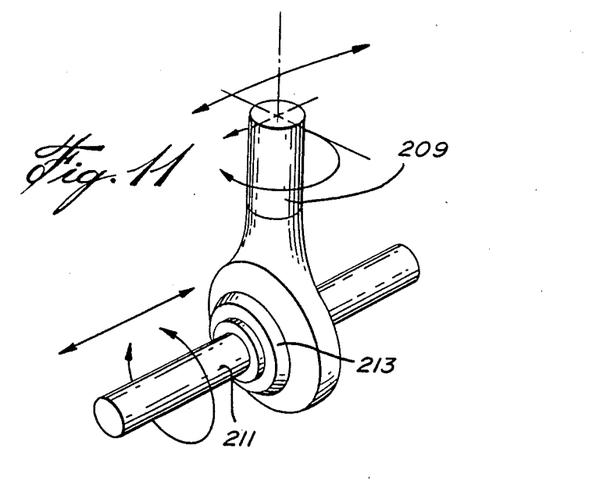
FIG. 11 illustrates in greater detail one of the beams of the invention dynanometer.

Although reference was made to dynanometers above, in accordance with a further aspect of the invention, there is provided a novel dynamometer, comprising a triple beam support system, illustrated in FIGS. 10 and 11 hereof. As seen in these Figures, the dynamometer comprises a supporting frame 201 which, in the illustrated embodiment, comprises a four walled structure. Disposed centrally of one wall is a first spherical or rectangular beam 203. Second and third rectangular or spherical beams 205 and 207 are disposed in the corners opposite the wall of the 203 beam.

As seen in FIG. 11, each beam comprises a vertical support portion 209 and horizontal deflection member 211. The vertical and horizontal members are joined by spherical/linear bearings 213. The bearings are the key to the proper operation of this triple beam system since they release all moments at the beams permitting the moments to be measured at various beams through their respective bending deflections, rather than being lost as axial beam compression or pure moments.

The beams are arranged such that the longitudinal axis of each deflection member 211 is the perpendicular bisector of a respective side of an equilateral triangle. This particular arrangement is convenient for subsequent analyses.

Supported at the top surfaces of the vertical members is a platform 215. The platform can be of any convenient shape, so long as it is supported by the top surfaces of the vertical members. In the illustrated embodiment, the platform 215 forms an equilateral triangle, and a beam is disposed at each corner of the triangle. The horizontal member of the beam is perpendicular to the side of the triangle opposite its corner.

Forces are measured by their application through the platform 215. These forces result in the deflection of the beams. The deflections are measured as an indicator of the forces.

Although in the illustrated embodiment the beams are at the corners of an equilateral triangle, any arrangement of three beams where there are no two redundant directions of deflections are permissible for two reasons:

(a) Such an arrangement will provide a rigid mechanical mechanism; and (b) The minimum of six non-redundant forces required for the solution of the equilibrium equations will be measured.

Devices, illustrated schematically at 217 and 219 with respect to beam 203, 221, 223 with respect to beam 207 and 225, 227 with respect to beam 205 are used to measure the deflection of the beams. The devices can comprise conventional displacement transducer devices and they would be mounted onto the rigid support frame and in such a manner that deflections in only the two planes of interest are measured for each beam. The resulting force measurements would be the minimum required to fully define all the external forces and moments acting on the platform. The necessary formulations for equilibrium of rigid body are the subject of numerous engineering text.

Conventional displacement transducers which can comprise the items 217 to 227 are:
  Capacitance gauge
  Linear variable differential transformer (LVDT)
  Hall effect detector
  Reflected/interrupted light intensity
  Rectilinear potentiometer.

With the set-up as illustrated, the deflections for each beam will be resolved in two directions through each beam. One direction is parallel to the axis of the vertical member and consists of the forces labelled F2, F4, F6, and the other direction is perpendicular to the first direction as illustrated by the arrows labelled F1, F3 and F5. The devices 217, 221 and 227 measure the forces in the directions F2, F4 and F6, while the devices 217, 223 and 225 measure the forces in the direction F1, F3 and F5.

When a force is applied to the platform 215, depending on the magnitude of the force and the direction of the application thereof, the beams 203, 205 and 207 will be deflected by different amounts. The magnitudes of deflection are resolved in the two directions as above-described, and the magnitudes in the respective directions are measured by the devices 217 to 227. Using this technology and well-known mathematical vector transformations, the force applied at the platform can be calculated.

Although particular embodiments have been described, this was for the purpose of illustrating but not limiting the invention. Various modifications, which will come readily to the mind of one skilled in the art, are within the scope of the invention as defined in the appended claims.

We claim:

1. A motion module/digitizer combination comprising:
   an elongated member having a first end and a second end and comprising a first link arm and a second link arm and means movably connecting said first link arm to said second link arm so as to permit translational motion between said first end and said second end, said means for connecting being disposed intermediate said first and second ends, said means also including first transducer means for measuring said translational motion;
   first mounting means at said first end for mounting said first end at a first point, body or co-ordinate system;
   second mounting means at said second end for mounting said second end at a second point or body;
   second transducer means at said first end for measuring three dimensional rotational motion of said first link arm relative to said first point or body;
   third transducer means at said second end for measuring three dimensional rotational motion of said second link arm relative to said second point or body;
   characterized in that said second link arm comprises a detachable portion and a non-detachable portion, said detachable portion of said second link arm being detachable from the non-detachable portion of said second link arm and said second mounting means;
   means connectable to the non-detachable portion of said second link arm;
   whereby, the combination of said first link arm, the non-detachable portion of said second link arm and said means connectable, can be used to measure the position in space of third, fourth, fifth . . . nth points or combinations thereof;
   and whereby, when said non-detachable portion of said link arm is reattached to said detachable portion of said second link arm and said mounting means, measurements can be performed to determine the position or motion in space of said second point or body relative to the position of said first point, body or co-ordinate system or said third, fourth, fifth . . . nth points, or positions of the second body, or combinations thereof.

2. A combination as defined in claim 1 wherein said first, second and third transducers comprise rotary transducers, the rotational axis of said rotary transducers being at right angles to the longitudinal axes of adjacent ones of said links, the longitudinal axes of said links running through said centers of rotation.

3. A combination as defined in claim 2 wherein said second transducer has an axis of rotation, and further including;
   a fourth rotary transducer having an axis of rotation and being disposed at said first end of said second transducer such that the axis of rotation of said second transducer is at right angles to the axis of rotation of said fourth transducer;
   the center of rotation of said fourth transducer being in line with the center of rotation of said second transducer.

4. A combination as defined in claim 3 wherein said third transducer has an axis of rotation and including a fifth rotary transducer having an axis of rotation and being disposed at said second end of said third transducer such that the axis of rotation of the fifth transducer is at right angles to the axis of rotation of said third transducer;
   the center of rotation of said fifth transducer being in line with the center of rotation of said third transducer;

a sixth rotary transducer having an axis of rotation, the axis of rotation of said sixth transducer being at right angles to the axis of rotation of said third transducer and said fifth transducer;

the center of rotation of said sixth transducer and said third transducer being in line.

5. A combination as defined in claim 4 wherein said first mounting means is attached to said fourth transducer and wherein said second mounting means is attached to said sixth transducer.

6. A combination as defined in claim 5 and including a data processor;

conductive means leading from said first, second, third, fourth, fifth and sixth transducers to said data processor;

whereby signals from said transducers can be analyzed by said data processor.

* * * * *